United States Patent [19]

Schneider

[11] Patent Number: 4,537,723

[45] Date of Patent: Aug. 27, 1985

[54] DERIVATIVES OF LEUKOTRIENES A AND C

[75] Inventor: William P. Schneider, Kalamazoo Township, Kalamazoo County, Mich.

[73] Assignee: The Upjohn Company, Kalamazoo, Mich.

[21] Appl. No.: 545,107

[22] Filed: Oct. 24, 1983

Related U.S. Application Data

[63] Continuation of Ser. No. 345,896, Feb. 4, 1982, abandoned.

[51] Int. Cl.$^3$ .................. C07C 163/00; C07C 149/40
[52] U.S. Cl. ............................ 260/400; 260/410.9 R; 260/413; 560/124; 562/506; 549/561
[58] Field of Search ................. 260/400, 410.9 R, 413

[56] References Cited

FOREIGN PATENT DOCUMENTS 68739 2/1983 European Pat. Off. ......... 260/404.5
118555 1/1982 Japan ................................ 260/404.5

OTHER PUBLICATIONS

Proc. Nat'l. Acad. Sci. U.S.A., Contractile Activities of Structural Analogs of Leukotrienes C and D: Role of the Polar Substituents, Lewis et al., 78: 4579, (1981).
Proc. Nat'l. Acad. Sci. U.S.A., Contractile Activities of Structural Analogs of Leukotrienes C and D: Necessity of a Hydrophobic Region, Drazen et al. 78: 3195, (1981).
Tetra. Lett., The Stereospecific Synthesis of Leukotriene A$_4$ (LAT$_4$), 5-Epi-LTA$_4$, 6-EPI-LTA$_4$, and 5-EPI, 6-EPI-LTA$_4$, Rokach et al., 22: 2759, (1981).
Tetra. Lett., A C-Glycoside Route to Leukotrienes, Rokach et al., 22: 2763, (1981).
Tetra. Lett., The Preparation of Octahydro Leukotrienes C, D, and E Via A Stereoselective Sulfenyllactonization Reaction, Rokach et al., 22: 4933, (1981).
Life Sci., Contractile Activities of Leukotrienes C$_4$ and D$_4$ on Vascular Strips from Rabbits, 29: 1325, (1981).
Prostaglandins, Leukotriene B$_4$: An Inflammatory Mediator in Vivo, Bray et al., 22: 213, (1981).
Tetra. Lett., Synthesis of Three Potential Inhibitors of the Biosynthesis of Leukotrienes A–E, Corey et al., 21: 4243, (1980).
Prasad, Inc. J. Chem. 7, 460, (1969).

*Primary Examiner*—Robert Gerstl
*Attorney, Agent, or Firm*—Lawrence T. Welch

[57] ABSTRACT

The present invention provides novel derivatives of leukotrienes A and C which are useful in inhibiting the smooth muscle contracting effects of SRS-A; inhibiting platelet aggregation; and inhibiting the biosynthesis of thromboxane A$_2$.

5 Claims, No Drawings

DERIVATIVES OF LEUKOTRIENES A AND C

BACKGROUND OF THE INVENTION

The present invention provides novel compositions of matter. In particular, the present invention provides novel derivatives of the leukotrienes. Most particularly, the present invention provides novel derivatives of leukotrienes A and C.

The leukotrienes are a class of unsaturated fatty acid compounds which are derived from arachadonic acid by the action of lipoxygenase. See, e.g., Samuelsson, Trends in Pharmacological Sciences, 5:227 (1980); and Samuelsson, et al., Annu. Rev. Biochem. 47:997–1029 (1978). This pathway is depicted in Chart D. For a discussion of leukotriene nomenclature, see Samuelsson, et al., Prostaglandins, 19:645 (1980).

The leukotrienes have been discovered as potent constrictors of human bronchi. That is, certain leukotrienes are mediators of the action of slow-reacting substance of anaphylaxis (SRS-A). See, e.g., Dahlen, Nature, 288:484 (1980). These compounds are therefore important mediators of bronchoconstriction in humans.

The role of leukotrienes as agonists in immediate hypersensitivity and other pathological conditions has led to research into inhibitors of leukotriene biosynthesis and leukotriene antagonists. See, e.g., Corey, et al., Tet. Lett. 21:4243 (1980).

Surprisingly and unexpectedly the leukotriene derivatives disclosed herein have been found to be leukotriene antagonists and inhibitors of SRS-A formation. They are also thromboxane synthetase inhibitors.

PRIOR ART

Certain leukotriene analogs are known. Drazen, et al., Proc. Nat'l. Acad. Sci. U.S.A. 78:3195 (1981) and Lewis, et al., Proc. Nat'l. Acad. Sci. U.S.A. 78:4579 (1981) disclose certain analogs of leukotrienes C, D and E which are disclosed as having contractile activity on guinea pig pulmonary parenchymal strips and guinea pig ileum. The contractile activities of leukotrienes $C_4$ and $D_4$ are also disclosed in Kito, et al., Life Sciences, 29:1325 (1981). The inflammatory action of leukotriene $B_4$ is disclosed in Bray, et al., Prostaglandins, 22:213 (1981). Core, et al., Tet. Lett. 21:4243 (1980) discloses two eicosenoic acids and one episulfide derivative as "potential" inhibitors of the biosynthesis of leukotrienes A-E. Rokach, et al., in Tet. Lett., 22:2759 (1981) discloses the stereospecific synthesis of leukotrienes $A_4$; 5-epi-$A_4$; 6-epi-$A_4$; and 5-epi, 6-epi-$A_4$. Three isomers of 7-hydroxy-5,6-epoxy heptanoic acid are disclosed in Rokach, Tett. Lett., 22:2763 (1981). Octahydro derivatives of leukotrienes $C_4$, $D_4$ and $E_4$ are disclosed in Rokach, Tett. Lett. 22:4933 (1981).

SCOPE OF THE INVENTION

The present invention provides
(a) a compound of the formula I
wherein $A_1$ is
  (1) —$CH_2$—$CH_2$—, or
  (2) trans—CH=CH—;
wherein $R_1$ is
  (1) hydrogen,
  (2) $C_1$—$C_3$ alkyl, or
  (3) a pharmacologically acceptable cation;
wherein $Z_1$ is
  (1) —O—, or
  (2) —CH(COO$R_2$)—, wherein $R_2$ is hydrogen or ($C_1$-$C_3$)alkyl;
wherein m is an integer from 3 to 7, inclusive, and wherein n is an integer from 7 to 13, inclusive; with the proviso that when $Z_1$ is —O—, $A_1$ is trans—CH=CH— and
(b) a compound of the formula II
wherein $A_1$ is
  (1) —$CH_2$—$CH_2$—, or
  (2) trans—CH=CH—;
wherein $R_1$ is
  (1) hydrogen,
  (2) ($C_1$-$C_3$)alkyl, or
  (3) a pharmacologically acceptable cation;
wherein one of $X_1$ and $Y_1$ is hydroxy and the other is
  (1) —S—$C_6H_5$, or
  (2) —Se$C_6H_5$;
wherein m is an integer from 3 to 7, inclusive; and wherein n is an integer from 7 to 13, inclusive.

The wavy line which connects certain substituents is meant to encompass both stereochemical configurations at that position. Compounds having either configuration are claimed as part of this invention.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 13 carbon atoms, inclusive, are methyl, ethyl, propyl, butyl, pentyl, hexyl, heptyl, octyl, nonyl, decyl, undecyl, dodecyl, tridecyl and isomeric forms thereof.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are
methylamine,
dimethylamine,
trimethylamine,
ethylamine,
dibutylamine,
triisopropylamine,
N-methylhexylamine,
decylamine,
dodecylamine,
allylamine,
crotylamine,
cyclopentylamine,
dicyclohexylamine,
benzylamine,
dibenzylamine,
α-phenylethylamine,
β-phenylethylamine,
ethylenediamine, diethylenetriamine,
and the like aliphatic, cycloaliphatic, araliphatic amines containing up to and including about 18 carbon atoms, as well as heterocyclic amines, e.g.,
piperidine,
morpholine,
pyrrolidine,
piperazine,
and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g.,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

The compounds of the present invention will be named herein as fatty acids, using the Chemical Abstracts numbering system (see Naming and Indexing of Chemical Substances for Chemical Abstracts during the Ninth Collective Period (1972–1976), a reprint of section IV from the Volume 76 Index Guide.)

As noted, compounds of this invention are useful to inhibit the formation of slow reacting substance—anaphylaxis (SRS-A) and thus its smooth muscle contracting effects, and to inhibit the biosynthesis of thromboxane $A_2$.

As an example of the SRS-A inhibitory activity of the compounds of this invention, several of these compounds were evaluated in a standard laboratory test. This test is conducted in rat mononuclear cells incubated in the presence of cysteine and challenged with a calcium ionophore (which induces SRS-A formation). In this test system, two of these compounds, the isomers of 1-carboxy-3-N-octylcyclopropane-2-octanoic acid. (Example 4 below), totally inhibited the synthesis of SRS-A at a concentration of 10 $\mu$g/ml.

In another test system, these compounds were both greater than 97 percent effective in preventing the formation of thromboxane $B_2$ ($TXB_2$) at a dose of 10 $\mu$g/ml.

Similarly, 9-hydroxy-10-phenylselenyloctadecanoic acid and 9-phenylselenyl-10-hydroxyoctadecanoic acid (Example 5) were 100% effective in preventing the synthesis of SRS-A at 10 $\mu$g/ml and both were at least 95% effective in preventing $TBX_2$ synthesis at 10 $\mu$g/ml.

Thus, these compounds are useful in the treatment of asthma. For example, these compounds are useful as bronchodilators or as inhibitors of mediators such as SRS-A which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations, by inhalation in the form of aerosols or solutions for nebulizers; or by insufflation in the form of powder. Doses in the range of about 0.01 to 50 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

The novel compounds of this invention have been shown to be highly active as inhibitors of the thromboxane synthetase enzyme system. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per min until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred. For a fuller discussion of the utility of $TXA_2$ inhibitors, see, e.g., Derwent Farmdoc Nos. 18399B; 72896B; 72897B; 63409B; 03755C; 03768C; and 50111C.

Because these compounds are $TXB_2$ inhibitors, these compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds, in laboratory animals, e.g., cats, dogs, rabbits, monkeys, and rats, for these purposes in order to develop new methods and techniques for organ and limb transplants.

The most preferred use of these compounds is as SRS-A inhibitors, e.g., in the treatment of asthma.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl ester, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Compounds of formulas I and II wherein m is 7 and n is 5 are most preferred for optimal activity. Compounds of Formulas I and II wherein m is 11 and n is 3 are also preferred.

The compounds of the present invention are prepared by the methods depicted in Charts A–C. In the charts, m and n are integers as defined above.

Thus, in Chart A, an unsaturated alcohol of the formula X (e.g., 5-alkyn-1-ol) is reacted with a hydroxy-group protecting agent (e.g., dihydropyran) to yield the Formula XI tetrahydropyranyl ether. This compound is then reacted with an n-alkyl bromide of the Formula $CH_3(CH_2)_nCH_2Br$ to yield the Formula XII compound. The protecting group is removed by reacting this compound with acid, and the resulting alkynol of the formula XIII is hydrogenated using a palladium catalyst to yield the Formula XIV compound. The Formula XIV compound is oxidized by reacting it with a known oxidizing agent (e.g., Jones reagent-acidified chromic acid, see Journal of the American Chemical Society, 39 (1946)) to yield the Formula XV compound. This compound is treated with an alkyl diazoacetate to yield the Formula XVI compound, which may be subsequently hydrolyzed to the corresponding diacid. Alternatively, the Formula XV compound is reacted with phenylselenyl chloride or phenylthionyl chloride to yield the Formula XVII compound, which may be hydrolyzed to the corresponding acid.

Referring to Chart B, an unsaturated fatty acid (e.g., oleic acid) of the Formula XX is reacted with an alkyl diazoacetate to yield the Formula XXII compound, which may be further hydrolyzed to the diacid. Alternatively, the Formula XX compound is reacted with phenylselenyl chloride in the presence of silver trifluoroacetate to yield the Formula XXI compound.

In Chart C, a compound of the Formula XXX (e.g., the monomethyl ester of glutaric acid) is reduced by treating it with oxalyl chloride followed by hydrogenalysis in the presence of a palladium catalyst. The resulting compound is reacted with alkylmethylenetriphenylphosphorane to yield the Formula XXXI compound. This compound is then treated with potassium carbonate and hydrogen peroxide to yield the Formula XXXII epoxide, which is converted to the Formula XXXIII product by reaction with an appropriate Wittig reagent. This compound is then hydrolyzed to the corresponding acid of the Formula XXXIV.

These procedures are described more fully in the Examples set out below.

DESCRIPTION OF THE PREFERRED EMBODIMENTS

The present invention is more fully understood by the Examples given below.

Preparation 1: 5-Hexyn-1-ol Tetrahydropyranyl Ether

Refer to Chart A (conversion of Formula X to Formula XI).

A solution of 35 g of 5-hexyn-1-ol, 35 g dihydropyran and 200 mg pyridine hydrochloride in 150 ml methylene chloride was stirred overnight at 25° C. The reaction was determined to be complete by thin-layer chromatography (TLC). The mixture was washed with sodium bicarbonate and saturated sodium chloride and then dried with sodium sulfate. This solution was passed through a short column of silica gel to remove color, evaporated, and Skellysolve B, (a commercial mixture of essentially n-hexane, B.P. 60°–68° C. (SSB)) was added to the residue and the remaining solvent was removed in vacuo. The NMR (CDCl$_3$, $\delta$) peaks observed were: 4.6, 4.1–3.2, 2.4–2.1, and 1.9. TLC analysis revealed an Rf of 0.55 in 25% ethyl acetate:SSB.

Preparation 2: 5-Eicosyn-1-ol Tetrahydropyranyl Ether

Refer to Chart A (conversion of Formula XI to Formula XII).

To 185 ml liquid ammonia was added 50 mg ferric nitrate, and then 1.44 g lithium wire in portions. After the blue color was completely gone, 26.7 g of hexynol tetrahydropyranyl in 82 ml of diethyl ether was added. After stirring for 0.5 hour a solution of 55 g n-tetradecyl bromide in 82 ml ether was added. The resulting mixture was stirred overnight while the ammonia was allowed to slowly evaporate through the condensor. Water was added, the products were extracted with ether, washed, dried, evaporated, and chromatographed on 2 kg silica gel, eluting with 5–20% ethyl acetate-SSB. Early fractions contained mostly unreacted tetradecyl bromide. Fractions 22–31 contained 13.05 g of titled product. Later fractions contained recovered hexynol THP.

The NMR peaks (CDCl$_3$, $\delta$) observed were: 4.6, 4.0–3.2, 2.1, and 0.9.

TLC analysis revealed an Rf of 0.71, in 25% ethyl acetate-SSB.

Preparation 3: 5-Eicosyn-1-ol and 5-Eicosen-1-ol

Refer to Chart A (conversion of Formula XII to Formula XIII).

Part A A solution of 1 g of Preparation 2 in 25 ml methanol was treated with 100 mg p-toluenesulfonic acid at 25° C. until conversion to a more polar product (Rf 0.28 in 25% ethylacetate/SSB) was complete (about 30 min). Sodium bicarbonate was added and the methanol was removed in vacuo. Extraction with ethyl acetate, drying and evaporation gave 736 mg of the above alochol which crystallized on standing, m.p. 45°–48° C.

The NMR (CDCl$_3$, $\delta$) peaks observed were: 3.7, 2.18, and 0.9.

Mass spectral analysis revealed peaks at m/e 294, 250, 208, 149, 135, 121, 111, 97, 94, 79, 68, 67, 57, and 55.

Part B (Conversion of Formula XIII to Formula XIV).

This material was dissolved in 15 ml hexane and hydrogenated with 33 mg of a Lindlar catalyst (a mixture of Pd, CaCO$_3$, and PbO made as described in Org. Synthesis 46, 89 (1966)). A total of 60.4 ml hydrogen was absorbed in 30 min. Filtration and evaporation gave 786 mg of 5-eicosen-1-ol, Rf 0.37 (25% ethyl acetate-Skellysolve B).

NMR (CDCl$_3$, $\delta$) peaks were observed at 5.4, 3.67, 2.7, and 0.9.

Preparation 4: 5-Eicosenoic Acid and Methyl 5-Eicosenoate

Refer to Chart A (conversion of Formula XIV to Formula XV).

The 786 mg of 5-eicosen-1-ol from Preparation 3 was dissolved in 75 ml acetone, cooled in ice, and treated with 1.33 ml of Jones reagent. After 15 min 3 ml isopropyl alcohol was added and when the color changed to blue the mixture was concentrated in vacuo and extracted with ethyl acetate. This was washed with 1N HCl and then with brine, dried and evaporated. Chromatography of a 158 mg. sample of the crude acid on approximately 20 g of acid-washed silica gel and elution with 12.5–25% ethyl acetate-SSB gave 139 mg of the desired acid.

The NMR (CDCl$_3$, $\delta$) absorptions observed were: 11.1, 5.7–5.0, 2.6–1.8, and 0.9.

This material was converted to the methyl ester with excess etheral diazomethane.

Gas chromatograph-mass spectroscopy (GC-MS) on a 6'1% SE column run from 30, 180°–260° C. at 10°/min showed one peak, at 5 min retention time, with a slight shoulder on the trailing edge (the trans isomer), with the same retention time and mass spectrum as an authentic sample prepared from cis-5-eicosenoic acid with diazomethane. The $^{13}$C NMR spectrum showed two major olefinic protons and two minor ones (approximately 10% of the major peaks), the latter evidently due to the trans isomer.

The NMR spectrum was the same as the above acid except for a peak at 3.68 $\delta$ (3 t) for OCH$_3$.

EXAMPLE 1

Threo-5-Hydroxy-6-Phenylselenyl-eicosanoic Acid
(Formula II: n is 11; A$_1$ is —CH$_2$—CH$_2$—, X$_1$ is —SeC$_6$H$_5$; Y$_1$ is hydroxy; R$_1$ is hydrogen; and m is 3)

Refer to Chart A (conversion of Formula XV to Formula XVIII).

A procedure similar to that of Nicolaou, et al., J. Am. Chem. Soc. 101:3884 (1979) was used. A solution of 1 g of largely cis 5-eicosenoic acid (Preparation 4) in 16 ml methylene chloride and 0.45 ml triethylamine at −78° C. was treated with 683 mg of phenylselenyl chloride. The solution was allowed to warm slowly to room temperature over about 1 hr. The reaction mixture was poured onto a column of 100 g, silica gel in CH$_2$Cl$_2$ and eluted with 10–25% ethyl acetate-CH$_2$Cl$_2$. Fractions 15–28 gave 570 mg of the lactone.

NMR (CDCl$_3$, $\delta$) peaks were observed at 7.8–7.15, 3.25, 2.5, and 0.9.

This material was hydrolyzed in 25 ml methanol with 1.23 ml sodium methoxide and 5 ml H$_2$O for 1 hr at 25° C. The mixture was acidified with 1N HCl, concentrated to remove methanol and extracted with ethyl acetate which was washed, dried, and evaporated. Chromatography on 75 g acid-washed silica gel and elution with 10–25% ethyl acetate-SSB gave 415 mg of pure titled product.

NMR (CDCl$_3$. $\delta$) peaks were observed at 8.7–7.2, ca 6.95, 3.65, 2.35 and 0.9.

EXAMPLE 2

Threo-5-Hydroxy-6-Phenylthio eicosanoic Acid
(Formula II: n is 11; A$_1$ is —CH$_2$—CH$_2$—; X$_1$ —S—C$_6$H$_5$; Y$_1$ is hydroxy; R$_1$ is hydrogen; and m is 3)

Refer to Chart A (conversion of Formula XV to Formula XVIII).

One gram of the product of Preparation 4, in 15 ml CH$_2$Cl$_2$ and 0.55 ml triethylamine was stirred at 25° C. for 30 min, then cooled to −78° C. and 3 ml of C$_6$H$_5$SCl in CH$_2$Cl$_2$ (approximately 233 mg/ml) was added. The mixture was allowed to warm to room temperature, concentrated to one-third its volume and applied to a column of 80 g silica gel in CH$_2$Cl$_2$. Elution was with 0–40% ethyl acetate-CH$_2$Cl$_2$ and then with 5% acetic acid in ethylacetate. Fractions 21–29 contained 817 mg of the lactone. The NMR was similar to the selenium analog described in Example 2.

This material in 32 ml methanol was treated with 1.59 ml of 25% sodium methoxide in methanol and 6.5 ml water. After 2.5 hr at 25° work-up as in Example 3 gave a product which contained approximately 50% of the methyl ester by NMR. This was dissolved in 5 ml methanol and 5 ml 1N NaOH was added. The mixture was stirred under nitrogen one hr, concentrated in vacuo, acidified with 2 ml 3N HCl, extracted with ethyl acetate, washed with sodium chloride, dried and evaporated. Chromatography on 100 g acid-washed silia gel and elution with 10–25% ethyl acetate-SSB gave 327 mg of crystalline product. NMR of this was very similar to that of the selenium analog, Example 2, except that the two ortho protons of the phenyl ring were not as far downfield as those of the selenium compound. On standing this material relactonizes slowly.

The product was purified by gas chromatography. Mass spectral ions at m/e 432 (m-18), 401, 323, 291, 273, 249, 207, and 109 (base peak). A minor product (evidently the lactone) had ions at m/e 418 (m+), 333, 319, 207, 147, and 123.

EXAMPLE 3

2-Carboxy-3-Tetradecyl Cyclopropanebutanoic Acid
(Formula I: $A_1$ is —$CH_2$—$CH_2$—; n is 11; $Z_1$ is
—$COOCH_2CH_3$; and m is 3)

Refer to Chart A (conversion of Formula XV to Formula XVII).

Part A ($R_1$ is methyl, $R_2$ is ethyl).

A mixture of 500 mg of largely cis-5-eicosenoic acid methyl ester and 50 mg copper powder was heated at 100° while 2.25 ml of ethyl diazoacetate was slowly added over about 2 hr. After cooling, it was diluted with ethyl acetate, filtered, and chromatographed on 50 g silica gel, eluting with 10–30% ethyl acetate-SSB. Fractions 7–9, 163 mg was largely starting material, followed by fractions 10–15, 90 mg and fractions 17–20, 233 mg, which contained two isomers of the cyclopropane mixed ethyl and methyl esters described above, the latter also containing (as evidenced by NMR) diethyl fumarate derived from decomposition of ethyl diazoacetate.

Mass spectral analysis of fractions 10–15, revealed ions at m/e 410, 379, 364, 333, 322, 309, 291, 249, and 213.

GC-MS of fractions 17–20 contained the same peaks as above.

Part B ($R_1$ hydrogen, $R_2$ is ethyl).

The above procedure was repeated to give 188 mg of the first isomer and 422 mg of the second isomer, contaminated with diethyl fumarate. These were combined with the corresponding portions from the first run and heated at 100° at ca 1 mm pressure to remove the diethyl fumarate leaving 248 mg first isomer and 229 mg second isomer.

Part C ($R_1$ is hydrogen, $R_2$ is hydrogen).

These esters were separately hydrolyzed in 6 ml of methanol with 4 ml 1N sodium hydroxide at 25° for 1 hr, then concentrated to remove most of the methanol and stirred overnight. They were acidified with 3N hydrochloric acid, extracted with ethyl acetate, washed, and dried. The mixture was then chromatographed on 25 g acid-washed silica gel, eluting with 30–50% ethyl acetate-SSB. The first isomer fractions (6–8), yielded 66 mg of a mono-ethyl ester (the NMR ($CDCl_3$ peaks were 4.15 δ (2 q) and ca 1.3 δ (3t)), of the titled Formula I compound while later fractions contained 56 mg of the diacid.

Mass spectral analysis (of the dimethyl ester from diazomethane), reveals ions at m/e 396, 364, 335, 332, 295, 291, 249, 199, 167, 135, and 81.

From chromatography of the hydrolysate of the second isomer above was obtained 112 mg of diacid.

The mass spectrum was the same as above.

EXAMPLE 4

1-Carboxy-3-n-Octylcyclopropane-2-Octanoic Acid
(Formula I: $n_1$ is 5; $A_1$ is —$CH_2CH_2$—; $Z_1$ is
—$CH(COOR_2)$—; m is 7, and $R_1$ is hydrogen)

Refer to Chart B (conversion of Formula XX to Formula XXII).

Part A ($R_2$ is ethyl)

To 1.0 g methyl oleate and 100 mg copper powder at 100° was added slowly 4.5 ml ethyl diazoacetate. After 2 hr the mixture was cooled, filtered and chromatographed on 100 g silica gel and eluted with 0% ethyl acetate-SSB. Fractions 5–11 (25 ml) contained 1.234 g of a mixture of product and diethyl fumerate. This was rechromatographed on 2 Merck B, silica gel columns to give 211 mg of purified methyl, ethyl ester of above cyclopropane.

NMR ($CDCl_3$, δ) peaks were observed at 4.12, 3.68, 2.3 and 0.9.

Part B ($R_2$ is hydrogen).

This product was hydrolyzed in 5 ml of ethanol with 1 ml 45% potassium hydroxide at 25° overnight. This was acidified with 3N HCl extracted with ethylacetate, washed, dried, and chromatographed on 30 g acid-washed silica gel, eluting with 15–100% ethyl acetate-SSB. Fractions 13–18 (10 ml) contained 125 mg of monoethyl ester.

NMR ($CDCl_3$, δ) peaks were observed at 4.12, 2.3 and 0.9.

Fractions 24–38 contained 106 mg of titled acid. NMR ($CDCl_3$, δ) peaks were observed at 2.35, and 0.9; with no ester absorptions.

EXAMPLE 5

9-Hydroxy-10-Phenylselenyloctadecanoic Acid and
9-Phenylselenyl-10-Hydroxyoctadecanoic Acid
(Formula II: n is 5; $A_1$ is —$CH_2$—$CH_2$—; $X_1$ is —OH;
$Y_1$ is —$SeC_6H_5$ (or $X_1$ is $SeC_6H_5$ and $Y_1$ is OH); m is 7;
and $R_1$ is hydrogen).

Refer to Chart B (conversion of Formula XX to Formula XXI).

Using the procedure of H. Reich, J. Org. Chem. 39:428 (1974), 210 mg phenylselenyl chloride, 221 mg silver trifluoroacetate and 300 mg of methyl oleate was added to 5 ml dry benzene. After only a few minutes the precipitate was filtered, the filtrate evaporated, and chromatographed on Merck B column of silica gel, eluting with 10% ethyl acetate-SSB. Fractions 12–14 (10 ml) contained 280 mg of methyl esters of above compound. NMR ($CDCl_3$, δ) peaks were observed at 7.8–7.2, 3.68, 3.3, 2.3, and 0.9. The product had an Rf of 0.47 in 10% ethyl acetate-SSB.

This was dissolved in 5 ml ethanol, 1 ml 45% potassium hydroxide (aq) was added and stirred overnight at 25° under nitrogen. The mixture was acidified with 3N HCl, concentrated, extracted with ethyl acetate, washed with saturated sodium chloride, dried, and evaporated. Chromatography on 30 g acid-washed silica gel and elution with 15–100% ethylacetate-SSB gave two products; fractions 11–24, 47 mg and 25–40, 207 mg which were tentatively assigned structures of the Formula II, when $Y_1$ is OH and $X_1$ is —SeC$_6$H$_5$, and of the Formula II where $X_1$ is seC$_6$H$_5$ and $X_1$ is OH, respectively. NMR (CDCl$_3$) peaks observed for fractions 25–40 were 7.7–7.2 δ (5 m), 7.05 (2 m COOH, OH), 3.6 δ (1 m), 3.15 δ (1 m), 2.3 (2 t), 0.9 (3 t). NMR peaks for 11–24 were similar.

Preparation 6: Refer to Chart C (conversion of Formula XXX to Formula XXXI).

Part A Methyl-4-Formylbutyrate

The method of Burgstahler, et al., Synthesis 767 (1976) was used. A solution of 6.5 g of the monomethyl ester of glutaric acid in 35 ml toluene was treated with 3.36 ml oxalyl chloride and 50 μl dimethyl formamide. After 70 min it was evaporated in vacuo. Toluene was added and the mixture was concentrated in vacuo. The mixture was transferred to a Parr hydrogenation bottle in toluene. 500 mg of a 10% palladium-on-carbon catalyst and 4.5 ml 2,6-lutidine were added and hydrogenation at approximately 25 lb. H$_2$ pressure was carried out. After 3 hr uptake the ceased. The suspension was filtered, washed with 2M potassium sulfate, dried, and evaporated to yield 6.5 g of the formula XXX ester aldehyde.

NMR (CDCl$_3$, δ) peaks were observed at 9.7, 3.68, 2.7–2.2, and 2.2–1.8.

Part B Methyl-6-Formyl-5-Hexenoate

A solution of 2.5 g of the Formula XXX compound corresponding to the titled product of Part A, above, 6.5 formylmethylene triphenylphosphorane (see Tripett, J. Chem. Soc. 1266 (1961)) and 50 ml dry benzene was refluxed 4.5 hr. It was evaporated and chromatographed on 200 g silica gel, eluting with 2 1 20–50% ethyl acetate-SSB. Fractions 15–20 (50 ml) contained 1.42 g of Formula XXXI titled product.

NMR (CDCl$_3$, δ) peaks were observed at 9.6, 7.2–6.6, 6.4–5.8, 3.68, 2.7–2.2, and 2.2–1.7, revealing a probable cis, trans mixture. The product had an Rf of 0.55 in 50% ethylacetate-SSB.

Preparation 7: Methyl 5,6-Epoxy-6-Formylhexanoate

Refer to Chart C (conversion of Formula XXXI to Formula XXXII).

A solution of 700 mg of Preparation 6, Part B in 14 ml methanol was cooled in an ice-salt bath. The mixture was treated with 1.05 g potassium bicarbonate in 10.5 ml water followed by 1.75 ml of 30% hydrogen peroxide. After 4 hr the mixture was concentrated in vacuo, extracted with ethyl acetate, washed with saturated brine, sodium chloride dried and evaporated. TLC shows a spot at Rf 0.24 in 50% ethyl acetate-SSB in addition to starting unsaturated aldehyde and NMR shows reduced olefinic protons and new protons at ca 3.1 δ due to epoxide protons.

EXAMPLE 6

Methyl 5,6-Epoxy-7-Eicosenoate (Formula I: n is 11; A$_1$ is trans—CH=CH—; Z$_1$ is —O—; m is 3; and R$_1$ is methyl)

Refer to Chart C (conversion of Formula XXXII to XXXIII).

To a suspension of 2.52 g of triphenyl tridecylphosphonium bromide (prepared from and triphenylphosphine and tridecyl bromide refluxing in benzene for 70 hr) in 28 ml dry benzene was added 3.08 ml of 1.6 M n-butyl lithium. After 1 hr, a solution of 700 mg of the product of Preparation 7 in 5 ml benzene was added. After stirring at 25° for 1 hr water was added, and then ethyl acetate, and the organic phase washed with saturated salt, sodium chloride, dried, evaporated and chromatographed on 300 g. silica gel, eluting with 5–25% ethyl acetate-SSB in 50 ml fractions.

Fractions 20–23 contained 146 mg of the above product.

NMR (CDCl$_3$, δ) absorbances were found at 5.74, 7.5, 5.05, 3.68, 3.34, 2.82, 2.6–2.0, and 0.9.

EXAMPLE 7

5,6-Epoxy-7-Eicosenoic Acid Sodium Salt (Formula I: n is 11; A$_1$ is trans—CH=CH—; Z$_1$ is —O—; m is 3; and R$_1$ is sodium)

Refer to Chart C (conversion of Formula XXXIII to XXXIV).

A solution of 56 mg of the product of Preparation 9 in 0.5 ml methanol was treated with 1.68 ml 00.1 M sodium methoxide and 1 ml distilled water. This was stirred overnight, concentrated to remove the methanol, filtered, and the clear filtrate was lyophilized to give 25 mg of white powder. The NMR spectrum of a sample still showed the olefinic and epoxide protons but no OCH$_3$ remaining.

EXAMPLE 8

Following the proceding examples, and the procedures depicted in Charts A–C, and using the appropriate starting materials, all of the remaining compounds within the scope of this invention can be prepared. Thus, e.g., the following compounds can be prepared:
5,6-epoxy-7-docosenoic acid;
5,6-epoxy-7-heneicosenoic acid;
5,6-epoxy-7-nonadecenoic acid;
5,6-epoxy-7-octadecenoic acid;
5,6-epoxy-7-heptadecenoic acid;
5,6-epoxy-7-hexadecenoic acid;
5,6-epoxy-7-pentadecenoic acid;
5,6-epoxy-7-tricosenoic acid;
5,6-epoxy-7-tetracosenoic acid;
5,6-epoxy-7-pentacosenoic acid;
5,6-epoxy-7-hexacosenoic acid;
threo-5-hydroxy-6-phenylselenyl-docosanoic acid;
threo-5-hydroxy-6-phenylselenyl-heneicosanoic acid;
threo-5-hydroxy-6-phenylselenyl-nonadecanoic acid;
threo-5-hydroxy-6-phenylselenyl-octadecanoic acid;
threo-5-hydroxy-6-phenylselenyl-heptadecanoic acid;
threo-5-hydroxy-6-phenylselenyl-hexadecanoic acid;
threo-5-hydroxy-6-phenylselenyl-pentadecanoic acid;
threo-5-hydroxy-6-phenylselenyl-tricosanoic acid;
threo-5-hydroxy-6-phenylselenyl-tetracosanoic acid;
threo-5-hydroxy-6-phenylselenyl-pentacosanoic acid;
threo-5-hydroxy-6-phenylselenyl-hexacosanoic acid;
threo-5-hydroxy-6-phenylthio-docosanoic acid;
threo-5-hydroxy-6-phenylthio-heneicosanoic acid;
threo-5-hydroxy-6-phenylthio-nonadecanoic acid;
threo-5-hydroxy-6-phenylthio-octadecanoic acid;
threo-5-hydroxy-6-phenylthio-heptadecanoic acid;
threo-5-hydroxy-6-phenylthio-hexadecanoic acid;
threo-5-hydroxy-6-phenylthio-pentadecanoic acid;
threo-5-hydroxy-6-phenylthio-tricosanoic acid;
threo-5-hydroxy-6-phenylthio-tetracosanoic acid;
threo-5-hydroxy-6-phenylthio-pentacosanoic acid;
threo-5-hydroxy-6-phenylthio-hexacosanoic acid;
2-carboxy-3-pentadecyl cyclopropanebutanoic acid;
2-carboxy-3-tridecyl cyclopropanebutanoic acid;

2-carboxy-3-dodecyl cyclopropanebutanoic acid;
2-carboxy-3-undecyl cyclopropanebutanoic acid;
2-carboxy-3-decyl cyclopropanebutanoic acid;
2-carboxy-3-pentadecyl cyclopropanepentanoic acid;
2-carboxy-3-tridecyl cyclopropanepentanoic acid;
2-carboxy-3-dodecyl cyclopropanepentanoic acid;
2-carboxy-3-undecyl cyclopropanepentanoic acid;
2-carboxy-3-decyl cyclopropanepentanoic acid;
2-carboxy-3-tetradecyl cyclopropanepentanoic acid;
2-carboxy-3-pentadecyl cyclopropanehexanoic acid;
2-carboxy-3-tridecyl cyclopropanehexanoic acid;
2-carboxy-3-dodecyl cyclopropanehexanoic acid;
2-carboxy-3-undecyl cyclopropanehexanoic acid;
2-carboxy-3-decyl cyclopropanehexanoic acid;
2-carboxy-3-tetradecyl cyclopropanehexanoic acid;
2-carboxy-3-pentadecyl cyclopropaneheptanoic acid;
2-carboxy-3-tridecyl cyclopropaneheptanoic acid;
2-carboxy-3-dodecyl cyclopropaneheptanoic acid;
2-carboxy-3-undecyl cyclopropaneheptanoic acid;
2-carboxy-3-decyl cyclopropaneheptanoic acid;
2-carboxy-3-tetradecyl cyclopropaneheptanoic acid;
2-carboxy-3-pentadecyl cyclopropaneoctanoic acid;
2-carboxy-3-tridecyl cyclopropaneoctanoic acid;
2-carboxy-3-dodecyl cyclopropaneoctanoic acid;
2-carboxy-3-undecyl cyclopropaneoctanoic acid;
2-carboxy-3-decyl cyclopropaneoctanoic acid; and
2-carboxy-3-tetradecyl cyclopropaneoctanoic acid, as well as the corresponding esters and pharmacologically acceptable salts thereof.

FORMULAS

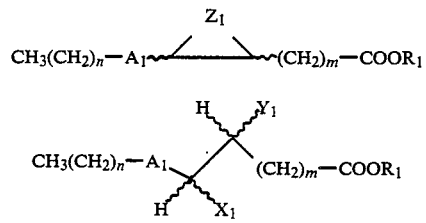

CHART A

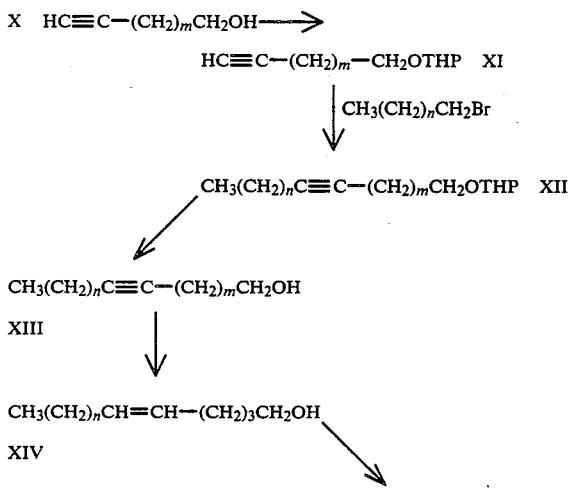

CHART A

-continued

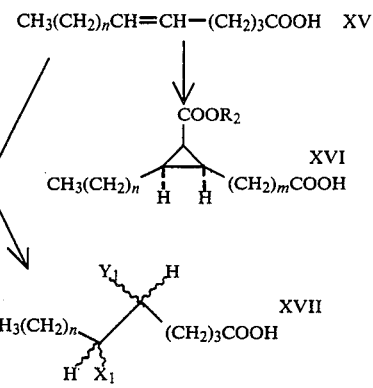

CHART B

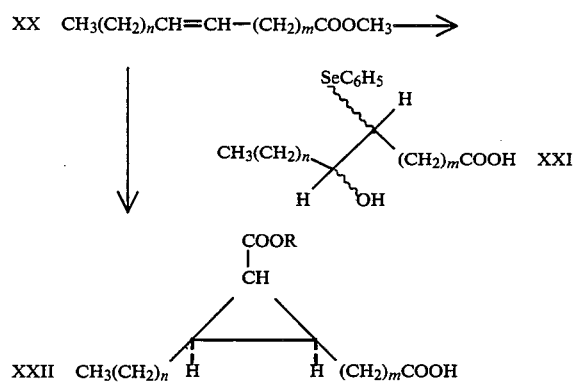

CHART C

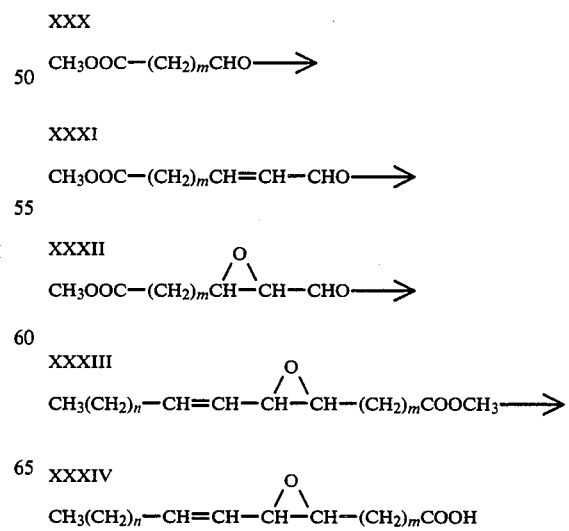

CHART D
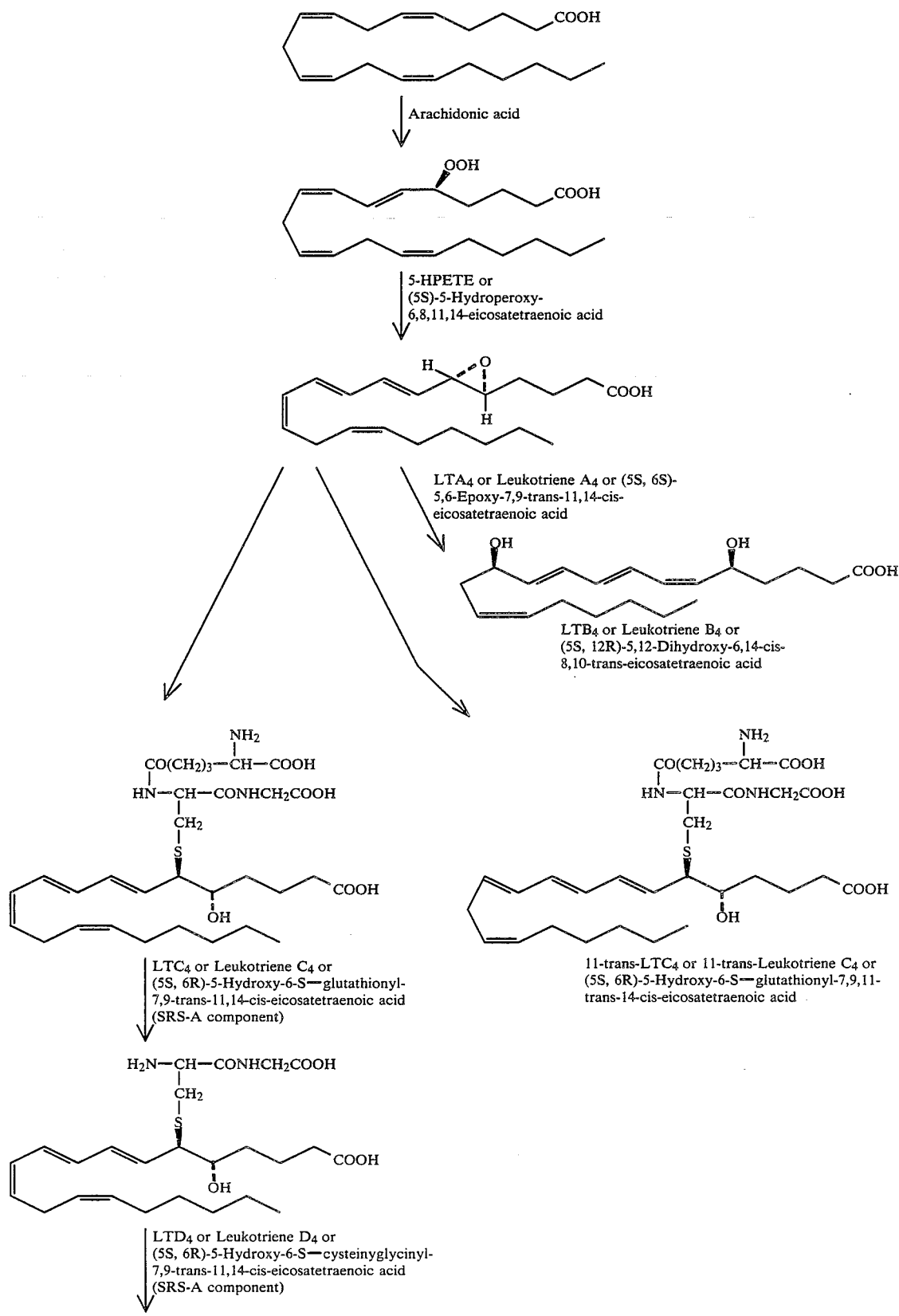

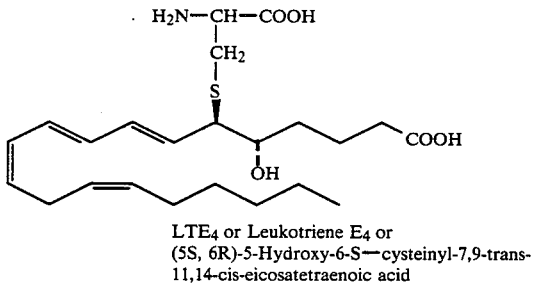

LTE₄ or Leukotriene E₄ or
(5S, 6R)-5-Hydroxy-6-S—cysteinyl-7,9-trans-11,14-cis-eicosatetraenoic acid

I claim:

1. A compound of the formula II

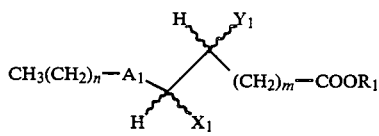

wherein $A_1$ is
  (1) —CH₂—CH₂—, or
  (2) trans—CH=CH—;
wherein $R_1$ is
  (1) hydrogen,
  (2) $C_1$-$C_3$ alkyl, or
  (3) a pharmacologically acceptable cation;
wherein one of $X_1$ and $Y_1$ is hydroxy and the other is
  (1) —S—C₆H₅, or
  (2) —SeC₆H₅;
wherein m is an integer from 3 to 7, inclusive; and
wherein n is an integer from 7 to 13, inclusive.

2. Threo-5-hydroxy-6-phenylselenyl-eicosanoic acid, a compound of claim 1.

3. Threo-5-hydroxy-6-phenylthio eicosanoic acid, a compound of claim 1.

4. 9-Hydroxy-10-phenylselenyloctadecanoic acid, a compound of claim 1.

5. 9-Phenylselenyl-10-hydroxyoctadecanoic acid, a compound of claim 1.

* * * * *

UNITED STATES PATENT OFFICE
CERTIFICATE OF CORRECTION

Patent No. 4,537,723                    Dated 27 August 1985

Inventor(s) W.P. Schneider

It is certified that error appears in the above-identified patent and that said Letters Patent are hereby corrected as shown below:

Column 7, line 34, "methanolwas" should read -- methanol was --.

Signed and Sealed this

Twenty-second Day of July 1986

[SEAL]

Attest:

DONALD J. QUIGG

Attesting Officer          Commissioner of Patents and Trademarks